(12) United States Patent
Stranne

(10) Patent No.: US 9,012,452 B2
(45) Date of Patent: Apr. 21, 2015

(54) PROCESSES FOR MAKING CYCLOPROPYL AMIDE DERIVATIVES AND INTERMEDIATES ASSOCIATED THEREWITH

(75) Inventor: Robert Stranne, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 13/579,605

(22) PCT Filed: Feb. 17, 2011

(86) PCT No.: PCT/SE2011/050171
§ 371 (c)(1),
(2), (4) Date: Mar. 14, 2013

(87) PCT Pub. No.: WO2011/102794
PCT Pub. Date: Aug. 25, 2011

(65) Prior Publication Data
US 2013/0172560 A1 Jul. 4, 2013

Related U.S. Application Data

(60) Provisional application No. 61/305,583, filed on Feb. 18, 2010.

(51) Int. Cl.
| A61K 31/497 | (2006.01) |
| C07D 295/104 | (2006.01) |
| A61K 31/4965 | (2006.01) |
| C07D 295/185 | (2006.01) |
| C07C 235/84 | (2006.01) |
| C07C 231/06 | (2006.01) |
| C07C 231/14 | (2006.01) |
| C07D 241/04 | (2006.01) |
| C07D 295/192 | (2006.01) |

(52) U.S. Cl.
CPC ........ C07D 295/192 (2013.01); A61K 31/4965 (2013.01); C07D 295/185 (2013.01); C07C 235/84 (2013.01); C07C 231/06 (2013.01); C07C 231/14 (2013.01); C07D 241/04 (2013.01)

(58) Field of Classification Search
CPC .......................... A61K 31/495; C07D 295/185
See application file for complete search history.

(56) References Cited

U.S. PATENT DOCUMENTS

| 3,331,830 A | 7/1967 | Stephen et al. |
| 3,449,427 A | 6/1969 | Kaiser et al. |
| 3,686,335 A | 8/1972 | Kaiser et al. |
| 3,697,506 A | 10/1972 | Butler |
| 4,432,987 A | 2/1984 | Barth et al. |
| 4,547,505 A | 10/1985 | Oepen et al. |
| 5,112,818 A | 5/1992 | Nakagawa et al. |
| 5,434,303 A | 7/1995 | Bohm et al. |
| 5,721,359 A | 2/1998 | Dunn et al. |
| 6,284,761 B1 | 9/2001 | Zhang et al. |
| 6,383,520 B1 | 5/2002 | Hirayama et al. |
| 6,521,619 B2 | 2/2003 | Link et al. |
| 6,544,996 B2 | 4/2003 | Zhang et al. |
| 6,861,432 B2 | 3/2005 | Cleve et al. |
| 7,053,089 B2 | 5/2006 | Claiborne et al. |
| 7,145,002 B2 | 12/2006 | Brands et al. |
| 7,217,716 B2 | 5/2007 | Claiborne et al. |
| 7,446,199 B2 | 11/2008 | Aronov et al. |
| 7,612,987 B2 | 11/2009 | Kurita et al. |
| 8,063,215 B2 | 11/2011 | Arnold et al. |
| 2004/0077618 A1 | 4/2004 | Bennani et al. |
| 2004/0209858 A1 | 10/2004 | Bennani et al. |
| 2005/0113309 A1 | 5/2005 | Kim et al. |
| 2005/0137201 A1 | 6/2005 | Aronov et al. |
| 2005/0143372 A1 | 6/2005 | Ghosh et al. |
| 2007/0054917 A1 | 3/2007 | Bruton et al. |
| 2007/0066821 A1 | 3/2007 | Allison et al. |
| 2007/0167436 A1 | 7/2007 | Nettekoven et al. |
| 2008/0021081 A1 | 1/2008 | Liu et al. |
| 2008/0242653 A1 | 10/2008 | Liu et al. |
| 2009/0076020 A1 | 3/2009 | Arnold et al. |
| 2009/0093525 A1 | 4/2009 | Du Bois et al. |
| 2009/0154067 A1 | 6/2009 | Kurita et al. |
| 2009/0181981 A1 | 7/2009 | Dunlap et al. |
| 2010/0216812 A1 | 8/2010 | Griffin |
| 2011/0201622 A1* | 8/2011 | Collins ............... 514/255.01 |
| 2011/0201623 A1 | 8/2011 | Uczynski |
| 2012/0065193 A1 | 3/2012 | Arnold et al. |

FOREIGN PATENT DOCUMENTS

| CA | 2374627 | 12/2000 |
| CN | 1341111 | 3/2002 |

(Continued)

OTHER PUBLICATIONS

Berlin et al., "Recent advances in the development of histamine H3 antagonists," Expert Opin. Ther. Patents, 2007, vol. 17(6), pp. 675-687.

Cho et al., "Convenient synthesis of optically active 1,2-diol monosulfonates and terminal epoxides via oxazaborolidine-catalyzed asymmetric borane reduction of α-sulfonyloxy ketones," J. Chem. Soc., Perkin Trans. 1, 2001, pp. 1204-1211.

De Esch et al., "Development of a pharmacophore model for histamine H3 receptor antagonists, using the newly developed molecular modeling program SLATE," J. Med. Chem., 2001, vol. 44, pp. 1666-1674.

(Continued)

*Primary Examiner* — Noble Jarrell
*Assistant Examiner* — John S Kenyon
(74) *Attorney, Agent, or Firm* — Ropes & Gray LLP

(57) ABSTRACT

Presented herein are processes for making cyclopropyl amide derivatives of formula I, and/or pharmaceutically acceptable salts thereof, and intermediates associated therewith. At least one cyclopropyl amide derivative of formula I, or pharmaceutically acceptable salt thereof is useful to treat at least one histamine H3 receptor associated condition.

28 Claims, No Drawings

(56) References Cited

FOREIGN PATENT DOCUMENTS

| | | |
|---|---|---|
| CN | 101384581 | 3/2009 |
| CN | 101462980 | 6/2009 |
| DE | 3418167 | 11/1985 |
| DE | 3600288 | 7/1987 |
| DE | 3618004 | 12/1987 |
| EP | 0120465 | 3/1984 |
| EP | 0129207 | 12/1984 |
| EP | 0234036 | 9/1987 |
| EP | 1849773 | 10/2007 |
| EP | 2039689 | 3/2009 |
| GB | 1086192 | 10/1967 |
| JP | 2002534421 | 10/2002 |
| RU | 2006125441 | 1/2008 |
| SU | 1297727 | 3/1987 |
| SU | 1542415 | 2/1990 |
| WO | WO9109594 | 7/1991 |
| WO | WO9303615 | 3/1993 |
| WO | WO9616040 | 5/1996 |
| WO | WO9637469 | 11/1996 |
| WO | WO9833784 | 8/1998 |
| WO | WO9837077 | 8/1998 |
| WO | WO9937304 | 7/1999 |
| WO | WO9942107 | 8/1999 |
| WO | WO0040572 | 7/2000 |
| WO | WO0076993 | 12/2000 |
| WO | WO0122963 | 4/2001 |
| WO | WO0151919 | 7/2001 |
| WO | WO0202522 | 1/2002 |
| WO | WO0208221 | 1/2002 |
| WO | WO02051781 | 7/2002 |
| WO | WO02068409 | 9/2002 |
| WO | WO03004480 | 1/2003 |
| WO | WO03014110 | 2/2003 |
| WO | WO03103666 | 12/2003 |
| WO | WO2004037769 | 5/2004 |
| WO | WO2004046110 | 6/2004 |
| WO | WO2004055010 | 7/2004 |
| WO | WO2004099156 | 11/2004 |
| WO | WO2005028475 | 3/2005 |
| WO | WO2005058884 | 3/2005 |
| WO | WO2006014168 | 2/2006 |
| WO | WO2006028290 | 3/2006 |
| WO | WO2006036015 | 4/2006 |
| WO | WO2006040192 | 4/2006 |
| WO | WO2006071730 | 7/2006 |
| WO | WO2006079916 | 8/2006 |
| WO | WO2006087169 | 8/2006 |
| WO | WO2006088075 | 8/2006 |
| WO | WO2006100591 | 9/2006 |
| WO | WO2006103544 | 10/2006 |
| WO | WO2006103545 | 10/2006 |
| WO | WO2006103555 | 10/2006 |
| WO | WO2007011065 | 1/2007 |
| WO | WO2007011623 | 1/2007 |
| WO | WO2007016496 | 2/2007 |
| WO | WO2007035425 | 3/2007 |
| WO | WO2007049123 | 5/2007 |
| WO | WO2007053386 | 5/2007 |
| WO | WO2007075895 | 7/2007 |
| WO | WO2007076140 | 7/2007 |
| WO | WO2007098536 | 9/2007 |
| WO | WO2007105729 | 9/2007 |
| WO | WO2007111921 | 10/2007 |
| WO | WO2007150010 | 12/2007 |
| WO | WO2008003702 | 1/2008 |
| WO | WO2008024284 | 2/2008 |
| WO | WO2008064817 | 6/2008 |
| WO | WO2008075068 | 6/2008 |
| WO | WO2008147864 | 12/2008 |
| WO | WO2008150364 | 12/2008 |
| WO | WO2008151957 | 12/2008 |
| WO | WO2009024823 | 2/2009 |
| WO | WO 2009024823 A2 * | 2/2009 |
| WO | WO2009109594 | 9/2009 |
| WO | WO2009135842 | 11/2009 |
| WO | WO2010012650 | 2/2010 |
| WO | WO 2010096011 A1 * | 8/2010 |
| WO | WO2011102793 | 8/2011 |
| WO | WO2011102794 | 8/2011 |
| WO | WO2011102795 | 8/2011 |

OTHER PUBLICATIONS

Halebian et al., "Pharmaceutical Applications of Polymorphism," J. Pharm. Sci. 1969, vol. 58, pp. 911-929, esp. p. 913.

Hamada et al., "A practical synthesis of optically active aromatic epoxides via asymmetric transfer hydrogenation of α-chlorinated ketones with chiral rhodium—diamine catalyst," Tetrahedron (2004), 60(34), pp. 7411-7417.

Hamada et al., "Practical Synthesis of Optically Active Styrene Oxides via Reductive Transformation of 2-Chloroacetophenones with Chiral Rhodium Catalysts," Organic Letters (2002), 4(24), pp. 4374-4376.

Ji, "The Histamine H3-receptor Ligands: Potential Therapeutic Uses," Pharm Care & Res, Sep. 2004, 4(3), pp. 183-187 (with English abstract).

Letavic et al., "Recent medicinal chemistry of the histamine H3 receptor," Progress in Medicinal Chemistry, 2006, vol. 44, pp. 181-206.

Mills et al., "SLATE: A method for the superposition of flexible ligands," Journal of Computer-Aided Molecular Design, 2001, vol. 15, pp. 81-96.

Ohkuma et al., "Asymmetric Hydrogenation of α-Chloro Aromatic Ketones Catalyzed by η6-Arene/TsDPEN—Ruthenium(II) Complexes," Organic Letters (2007), 9(2), pp. 255-257.

Pierson et al., "4-Hydroxyindole-2-carboxylic Acid Amides: Novel Histamine-3 Receptor Inverse Agonists for the Treatment of Obesity," J. Med. Chem. 2009, 52, pp. 3855-3868.

Pikal et al, "The Stability of Insulin in Crystalline and Amorphous Solids: Observation of Greater Stability for the Amorphous Form," Pharmaceutical Research, 1997, vol. 14, pp. 1379-1387, esp. p. 1379.

Sander et al., "Histamine H3 Receptor Antagonists to Clinics," Biol. Pharm. Bull., 2008, vol. 31(12), pp. 2163-2181.

Singh et al., "Development of a Practical, Safe, and High-Yielding Process for the Preparation of Enantiomerically Pure trans-Cyclopropane Carboxylic Acid," Organic Process Research & Development 2002, 6, pp. 618-620.

Watanabe et al., "Investigation of the Bioactive Conformation of Histamine H3 Receptor Antagonists by the Cyclopropylic Strain-Based Conformational Restriction Strategy," J. Med. Chem. 2010, vol. 53, pp. 3585-3593.

Watanabe et al., Poster "Development of potent histamine H3/H4 receptor ligands by the stereochemical diversity-oriented chiral cyclopropane-based conformational restriction strategy," Presented at 234th ACS National Meeting held in Boston Aug. 19-23, 2007.

Wijtmans et al., "Histamine H3 receptor ligands break ground in a remarkable plethora of therapeutic areas," Expert Opin. Investig. Drugs, 2007, vol. 16(7), pp. 967-985.

Wisdom et al., "Enzymatic synthesis of carbo-and heterocyclic aryl oxiranes," Speciality Chemicals Magazine, 27(8), 32-33(2007).

Yamaguchi et al., "Construction of a cis-Cyclopropane via Reductive Radical Decarboxylation. Enantioselective Synthesis of cis- and trans-1-Arylpiperazyl-2-phenylcyclopropanes Designed as Antidopaminergic Agents," J. Org. Chem., 2003, vol. 68, No. 24, pp. 9255-9262.

Zhang et al., "trans-1-[(2-Phenylcyclopropyl)methyl]-4-arylpiperazines: Mixed Dopamine D2/D4 Receptor Antagonists as Potential Antipsychotic Agents," J. Med. Chem., 2000, vol. 43, pp. 3923-3932.

API form screening and selection in drug discovery stage, PHARM STAGE, v. 6, No. 10, 2007, pp. 20-25.

Armarego et al. "Purification of Laboratory Chemicals", 5th Ed., Chapter 1, pp. 1-30, © 2003, Elsevier, Cornwall, GB.

Becke, "Density-functional thermochemistry. III. The role of exact exchange," J. Chem. Phys. 1993, 98(7), pp. 5648-5652.

Brittain et al., "Polymorphism in pharmaceutical solids," (1999) chapter 6, p. 236.

(56) References Cited

OTHER PUBLICATIONS

Byrn et al., "Pharmaceutical Solids: A Strategic Approach to Regulatory Considerations," Pharmaceutical Research, (1995), vol. 12, No. 7, pp. 945-954.

Caira, "Crystalline Polymorphism of Organic Compounds," Topics in Current Chemistry, Springer, Berlin, DE, vol. 198, Jan. 1, 1998, pp. 163-208.

Crystallization of Polymorphs and Pseudo-polymorphs and Its Control, PHARM STAGE, v. 6, No. 10, 2007 pp. 48-53.

Gennaro, "Remimgton Farmacia", Tome 2, Edition 19, Editorial Médica Panamericana, 1998, p. 2226, col. right and p. 2228, col. Left and right.

Gillaspy et. al., "A Simple Method for the Formation of Cyclopropylamines: The First Synthesis of Tricyclopropylamine," Tetrahedron Lett. 1995, 36 (41), pp. 7399-7402.

Hariharan et al., "The Influence of Polarization Functions on Molecular Orbital Hydrogenation Energies," Theor. Chim. Acta, 1973, 28, pp. 213-222.

Hickey et al, "Hydrates and Solid-State Reactivity: A Survey of β-Lactam Antibiotics," Journal of Pharmaceutical Sciences, vol. 96, No. 5, May 2007, pp. 1090-1099.

Jain et al., "Polymorphism in Pharmacy," Indian Drugs, (1986), vol. 23(6), pp. 315-329.

Kawaguchi et al., "Drug and Crystal Polymorphism," Life Engineering, 2002, v. 4, pp. 310-317.

Lee et al., "Development of the Colle-Salvetti correlation-energy formula into a functional of the electron density," Phys. Rev. B, 1988, 37(2), pp. 785-789.

Luo et al, "Research Progress of Histamine H3 Receptor and Its Relationship with Neurological Diseases," Acta Academiae Medicinae Zunyi, vol. 28, No. 6, Dec. 2005, pp. 569571.

Newman et al., "Solid-state analysis of the active pharmaceutical ingredient in drug product," Drug discovery today, (2003), vol. 8, No. 19, pp. 898-905.

Pitha et al., "Alkylating prazosin analog: irreversible label for alpha-1-adrenoceptors," J. Med. Chem., vol. 32, 1989, pp. 96-100.

Polymorphism in pharmaceutical solids, edited by H. G. Brittain, Marcel Dekker, D.J.W. (1999), Grant (chapter 1) p. 1-10; and Guillory (chapter 5) p. 183-226.

Report by the Council on Medical Service Facilities No. 568, 2001.

Singhal et al., "Drug Polymorphism and Dosage Form Design: A Practical Perspective," Advanced Drug Delivery Review, vol. 56, pp. 335-347, 2004.

Wu et al., "Research Progress of Histamine H3 Receptor Ligands," Chin Pharm J. Mar. 2007, vol. 42, No. 6, pp. 404-409.

Yamano, "Approach to Crystal Polymorph in Process Research of New Drug," J. Synth. Org. Chem., Jpn. V. 65, No. 9, 2007, pp. 907-913.

Zaragoza et al., "1-Alkyl-4-acylpiperazines as a New Class of Imidazole-Free Histamine H3 Receptor Antagonists," J. Med. Chem. 2004, 47, pp. 2833-2838.

* cited by examiner

PROCESSES FOR MAKING CYCLOPROPYL AMIDE DERIVATIVES AND INTERMEDIATES ASSOCIATED THEREWITH

CROSS-REFERENCE TO RELATED PATENT APPLICATIONS

This patent is a US National Stage under 35 U.S.C §371 of Int'l Patent Appl. No. PCT/SE2011/050171 (filed Feb. 17, 2011), which, in turn, claims priority under 35 U.S.C. §119(e) to U.S. Provisional Patent Appl. No. 61/305,583 (filed Feb. 18, 2010). The entire text of each of the above-referenced patent applications is incorporated by reference into this patent.

Presented herein are processes for making cyclopropyl amide derivatives of formula I, and/or pharmaceutically acceptable salts thereof, and intermediates associated therewith. At least one cyclopropyl amide derivative of formula I, or pharmaceutically acceptable salt thereof is useful to treat at least one histamine H3 receptor associated condition.

The histamine H3 receptor is of current interest in developing new medicaments. The H3 receptor is a presynaptic autoreceptor located both in the central and peripheral nervous systems, the skin, and in organs, such as, for example, the lung, the intestine, probably the spleen, and the gastrointestinal tract. Recent evidence suggests the H3 receptor has intrinsic, constitutive activity in vitro as well as in vivo (i.e., it is active in the absence of an agonist). Compounds acting as inverse agonists can inhibit this activity. The histamine H3 receptor has been shown to regulate the release of histamine and also of other neurotransmitters, such as, for example, serotonin and acetylcholine. Some histamine H3 ligands, such as, for example, a histamine H3 receptor antagonist or inverse agonist may increase the release of neurotransmitters in the brain, whereas other histamine H3 ligands, such as, for example, histamine H3 receptor agonists may inhibit the biosynthesis of histamine, as well as, inhibit the release of neurotransmitters. This suggests that histamine H3 receptor agonists, inverse agonists, and antagonists could mediate neuronal activity. As a result, efforts have been undertaken to develop new therapeutics that target the histamine H3 receptor.

U.S. patent application publication no. 2009/0076020 describes the synthesis of a number of cyclopropyl amide derivatives, such as, for example, 4-((trans)-2-[(4-cyclobutylpiperazin-yl)carbonyl]-cyclopropyl}-benzamide (enantiomer 1; Example 43). Improved processes of making these compounds would be advantageous, especially processes amenable to large scale synthesis.

Described herein are processes of making cyclopropyl amide derivatives of formula I and pharmaceutically acceptable salts thereof:

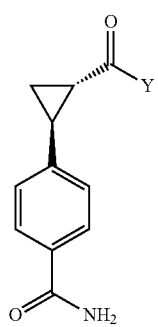

(I)

wherein Y is OH,

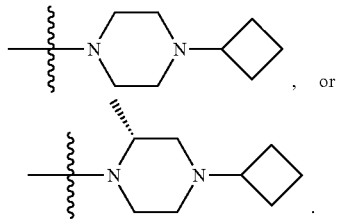

, or

Further described herein is a compound of Formula Ia, or a pharmaceutically acceptable salt thereof:

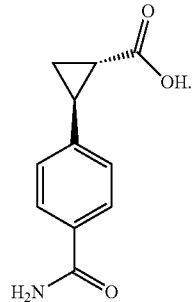

(Ia)

Throughout this disclosure it is to be understood that, where appropriate, suitable protecting groups may be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis," T. W. Green, P. G. M. Wuts, Wiley-Interscience, New York, (1999).

A transformation of a group or substituent into another group or substituent by chemical manipulation can be conducted on any intermediate or final product on the synthetic path toward the final product; the type of transformation is limited only by the inherent incompatibility of other functional groups contained in the molecule to the conditions or reagents employed in the transformation. Such inherent incompatibilities, and ways to circumvent them by carrying out appropriate transformations and synthetic steps in a suitable order, will be readily understood by one skilled in the art of organic synthesis.

Examples of transformations are given below, and it is understood that the described transformations are not limited only to the generic groups or substituents for which the transformations are exemplified. References and descriptions of other suitable transformations are given in "Comprehensive Organic Transformations—A Guide to Functional Group Preparations" R. C. Larock, Wiley VCH, $2^{nd}$ Edition (1999).

Examplary reaction conditions are given below, and it is understood that the describe reaction conditions are not limited only to the described reaction conditions. References and descriptions of other suitable reaction conditions are described in textbooks of organic chemistry, such as, for example, "Advanced Organic Chemistry", March $6^{th}$ Edition, Wiley Interscience (2007), and "Organic Synthesis", Smith, $2^{nd}$ Edition, McGraw Hill, (2001).

Techniques for purification of intermediates and final products include, for example, normal and reversed phase chromatography on column or rotating plate, recrystallization, distillation and liquid-liquid or solid-liquid extraction, each of which will be readily understood by one skilled in the art.

The term "amino-protecting group" refers to art-recognized moieties capable of attaching to an amino group so as to prevent the amino group from taking place in reactions occurring elsewhere on the molecule to which the amino group is attached. Acceptable amino-protecting groups, include but are not limited to, for example, amino-protecting groups described in "Protective Groups in Organic Synthesis", 4th edition, Wiley Interscience, 2006. The amino-protecting group may be, for example, a urethane type protective group (which is also referred to as a carbamate protective group), which includes but is not limited to, for example, arylalkyloxycarbonyl groups, such as, for example, benzyloxycarbonyl; and alkoxycarbonyl groups, such as, for example, methoxycarbonyl and tert-butoxycarbonyl. Typically, the amino-protecting group is tert-butoxycarbonyl.

In general, the compounds of formula I can be prepared in accordance with the following Schemes and the general knowledge of one skilled in the art and/or in accordance with the methods set forth in the Examples that follow. Solvents, temperatures, pressures, and other reaction conditions may readily be selected by one of ordinary skill in the art. Starting materials are commercially available or readily prepared by one skilled in the art.

The term "$C_{1-6}$alkyl" refers to a straight or branched chain alkane (hydrocarbon) radical containing from 1 to 6 carbon atoms. Exemplary "$C_{1-6}$alkyl" groups include, but are not limited to, for example, methyl; ethyl; propyl; isopropyl; 1-methylpropyl; n-butyl, t-butyl; isobutyl; pentyl; hexyl; and isohexyl.

Scheme 1

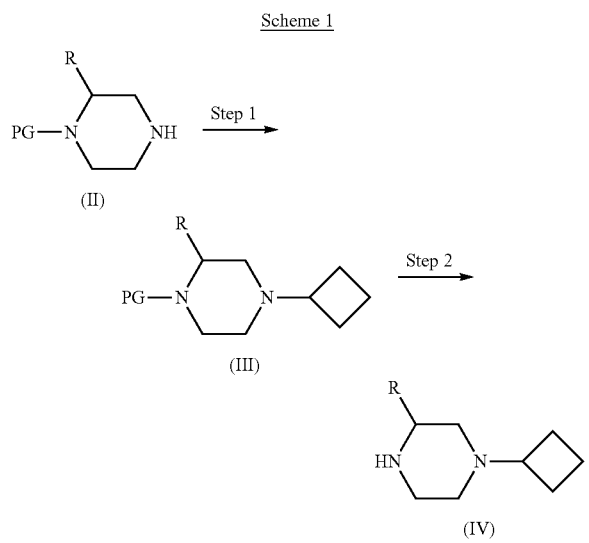

For the compounds depicted in Scheme 1, PG is an amino-protecting group; and R is H or a $C_{1-6}$alkyl.

In one embodiment, $C_{1-6}$alkyl is selected from methyl, ethyl, propyl, and isopropyl.

In another embodiment, the amino protecting group is tert-butoxycarbonyl.

In a further embodiment, R is H.

In a yet another embodiment R is methyl.

In an even further embodiment, the compounds of formula II, III and IV are compounds of formula IIa, IIb, IIIa, IIIb, IVa and IVb, respectively:

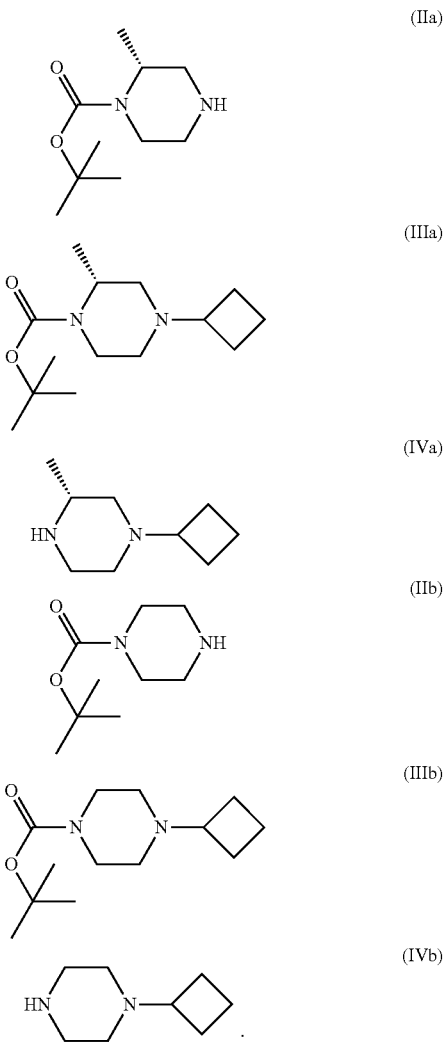

In still a further embodiment, the compounds of formula II, III and IV are selected from formula IIa, formula IIb, formula IIIa, formula IIIb, formula IVa, and formula IVb.

In yet still as further embodiment, compounds in accordance with formula II, III, or IV may be in the form of a suitable salt, such as, for example, the acetate or dihydrochloride. In certain embodiments, the compounds of formula IVa and IVb may be in the form of the dihydrochloride salt.

Step 1:

Compounds in accordance with formula III can be obtained by treating compounds in accordance with formula II with cyclobutanone and a suitable reducing agent, such as, for example, sodium triacetoxyborohydride or sodium cyanoborohydride, in a suitable solvent, such as for example, 1,2-dichloroethane, tetrahydrofuran, ethanol, or acetic acid, or a solvent mixture comprising two or more solvents, such as, for example, a solvent mixture comprising ethanol and acetic acid. Compounds in accordance with formula II are commercially available and include, for example, (R)-Boc-2-methylpiperazine, which is commercially available from Lanzhou Boc Chemical Co., and N-Boc-piperazine, which is commercially available from Sigma-Aldrich. In certain embodiments, the compounds in accordance with formula III are not isolated, but instead are carried through to step 2.

Step 2:

Compounds in accordance with formula IV can be obtained by treating compounds in accordance with formula III with a suitable reagent to deprotect the amino group, such as for example, an acid, such as for example, hydrochloric acid, trifluoroacetic acid, or sulfonic acid, in a suitable solvent, such as, for example, dioxane, dichloromethane, 2-propanol or a suitable mixture comprising two or more solvents, such as, for example, a solvent mixture comprising 2-propanol and toluene.

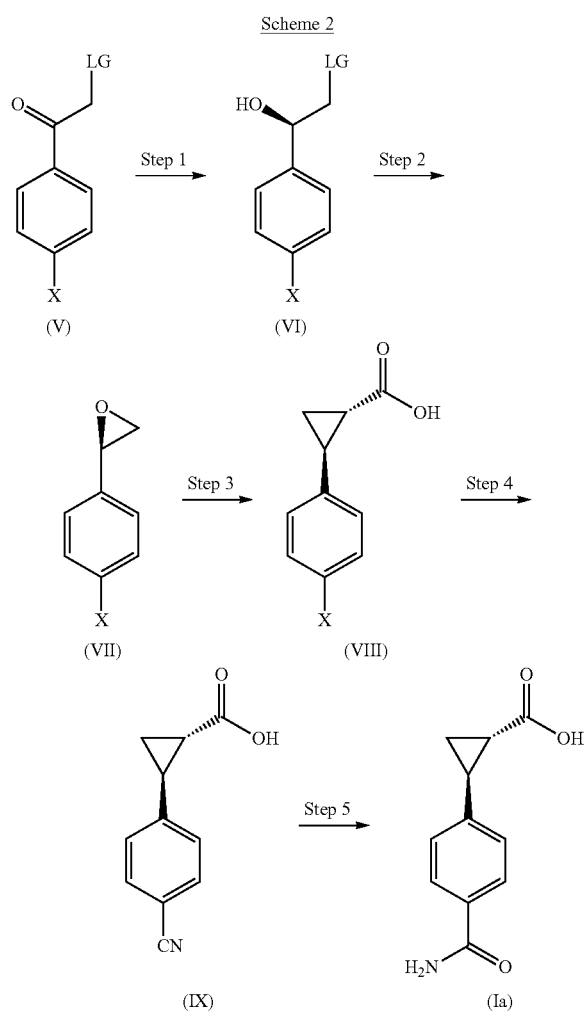

pound V by either enzymatic transformation, catalytic transfer hydrogenation or reduction using a chiral oxazaborolidine together with a reducing agent, followed by base treatment with or without the presence of a phase transfer catalyst in a suitable solvent. Descriptions of these transformations can be found, for example, in *Speciality Chemicals Magazine*, 27(8), 32-33 (2007); WO2008064817; Faming Zhuanli Shenqing, 101747211; WO 2006036015; WO 2006028290; WO 2007011065; *Organic Letters* (2002), 4(24), 4373-4376; WO 2002051781; *Tetrahedron* (2004), 60(34), 7411-7417; *Organic Letters* (2007), 9(2), 255-257; and *Journal of the Chemical Society*, Perkin Transactions 1 (2001), (10), 1204-1211.

In one embodiment, compounds in accordance with formula VI can be obtained by adding a compound in accordance with formula V, which is dissolved in a suitable solvent, such as, for example, tetrahydrofuran, 2-methyl-tetrahydrofuran, toluene, dichloromethane, or a mixture of two or more thereof, to a solution comprising i) a suitable reducing agent, such as, for example, borane*THF or borane dimethylsulfide in a suitable solvent, such as, for example, tetrahydrofuran, 2-methyl-tetrahydrofuran, toluene, dichloromethane, or a mixture of two or more thereof, and ii) a chiral oxazaborolidine, such as, for example, (R)-(+)-methyl-CBS-oxazaborolidine (CAS-No. 112022-83-0).

In another embodiment, compounds in accordance with formula VII can be obtained by treating a compound of formula VI in a suitable first solvent, such as, for example, dichloromethane, tetrahydrofuran, 2-methyl-tetrahydrofuran, or a mixture of two or more thereof, with a phase-transfer catalyst, such as, for example, an ammonium salt (e.g., methyl tributyl ammonium chloride or tetrabutylammonium chloride), a heterocyclic ammonium salt (e.g., 1,1'-dibenzyl-4,4'-bipyridinium dichloride, 1,2,3-trimethylimidazolium methyl sulfate), or a phosphonium salt (e.g., tetrabutylphosphonium chloride or tetraphenylphosphonium chloride), with a suitable base, such as, for example, sodium hydroxide diluted in a suitable second solvent, such as, for example, water. In one embodiment, the first and second solvent form two phases when mixed together.

In a yet another embodiment, compounds in accordance with formula VII can be obtained by treating a compound of formula VI with a suitable base, such as, for example, sodium hydroxide or lithium hydroxide, in a suitable solvent, such as, for example, methanol, ethanol, tetrahydrofuran, dioxane, water, or a mixture of two or more thereof. In a still further embodiment, the base is sodium hydroxide when X is Br and LG is Cl.

Compounds in accordance with formula V are commercially available and include 1-(4-Bromo-phenyl)-2-chloro-ethanone, which is commercially available from, for example, Jiangyan Keyan Fine Chemical Co. Ltd. Compounds in accordance with formula VII are commercially available and include (R)-2-(4-Bromo-phenyl)-oxirane, which is commercially available from, for example, American Custom Chemicals Corp.

In certain embodiments, compounds in accordance with formula VI are not isolated, but instead carried through to step 2. In certain embodiments, compounds in accordance with formula VII are not isolated, but instead carried through to step 3.

Step 3:

Compounds in accordance with formula VIII can be obtained, for example, from compounds in accordance with formula VII by methodology described, for example, in WO 2006087169 and *Org. Proc. Res. Dev.* 2002, 6, 618.

For the compounds depicted in Scheme 2, X is F, Cl, Br, or I; and LG is Cl, Br, I, tosylate, brosylate, nosylate, or mesylate.

In another embodiment, X is Cl, Br, or I and LG is Cl, Br, I, tosylate, brosylate, nosylate, or mesylate. In a further embodiment, X is Br. In a still further embodiment, LG is Cl. In yet another embodiment, LG is Cl, Br, I, or tosylate. In a yet still further embodiment, X is BR and LG is Cl.

Steps 1 and 2:

Compounds in accordance with formula VI (step 1) and VII (steps 1 and 2, in the latter case either stepwise or in a telescope procedure) can be obtained, for example, from com- In one embodiment, compounds in accordance with formula VIII can be obtained by preparing a solution of i) a suitable first base, such as, for example, alkyl lithium (e.g., n-hexyl lithium) in a suitable solvent, such as, for example, hexane, and ii) a suitable triC$_{1-6}$alkyl phosphonoacetate (e.g., triethyl phosphonoacetate, trimethyl phosphonoacetate, and methyl diethylphosphonoacetate) in a suitable solvent, such as, for example, tetrahydrofuran, 2-methyl-tetrahydrofuran, or mixture thereof, and combining therewith a compound in accordance with formula VII in a suitable solvent, such as, for example, tetrahydrofuran, 2-methyl-tetrahydrofuran, or mixture thereof. The resulting mixture is further treated with a suitable second base, such as, for example, sodium hydroxide or lithium hydroxide. Prior to the addition of the second base, an unisolated intermediate is formed containing an alkylester, such as, for example, ethyl ester where the free carboxylic acid group of the formula VIII compound is present. In one embodiment, the unisolated intermediate that is formed prior to the addition of the second base is isolated.

In a further embodiment, the compound in accordance with formula VIII is purified by recrystallization using a suitable solvent, such as, for example, ethanol, water, toluene, isooctane, or a mixture of two or more thereof.

In an embodiment where X is BR, the first base is n-hexyl lithium; the triC$_{1-6}$alkyl phosphonoacetate is triethylphosphonoacetate; and the second base is sodium hydroxide.

Compounds in accordance with formula V are commercially available and include (1S,2S)-2-(4-bromophenyl)cyclopropanecarboxylic acid, which is commercially available from, for example, BOC Sciences.

Step 4:

A compound in accordance with formula IX can be obtained by treating a compound in accordance with formula VIII in a suitable solvent, such as, for example, dimethylformamide with a suitable metal, such as zinc (e.g., zinc dust); a suitable catalyst, such as, for example, bis(tri-t-butylphosphine)palladium(0); and a suitable metal cyanide, such as, for example, zinc-(II)-cyanide.

In certain embodiments, compounds in accordance with formula IX are not isolated, but instead carried through to step 5.

Step 5:

A compound in accordance with formula Ia can be obtained by treating a compound in accordance with formula IX in a suitable solvent, such as, for example, water, with a suitable base, such as, for example, sodium hydroxide, and a suitable peroxide, such as, for example, hydrogen peroxide, followed by treatment with a suitable acidic solution, such as, for example, an aqueous solution of sodium hydrogen sulfate.

Scheme 3

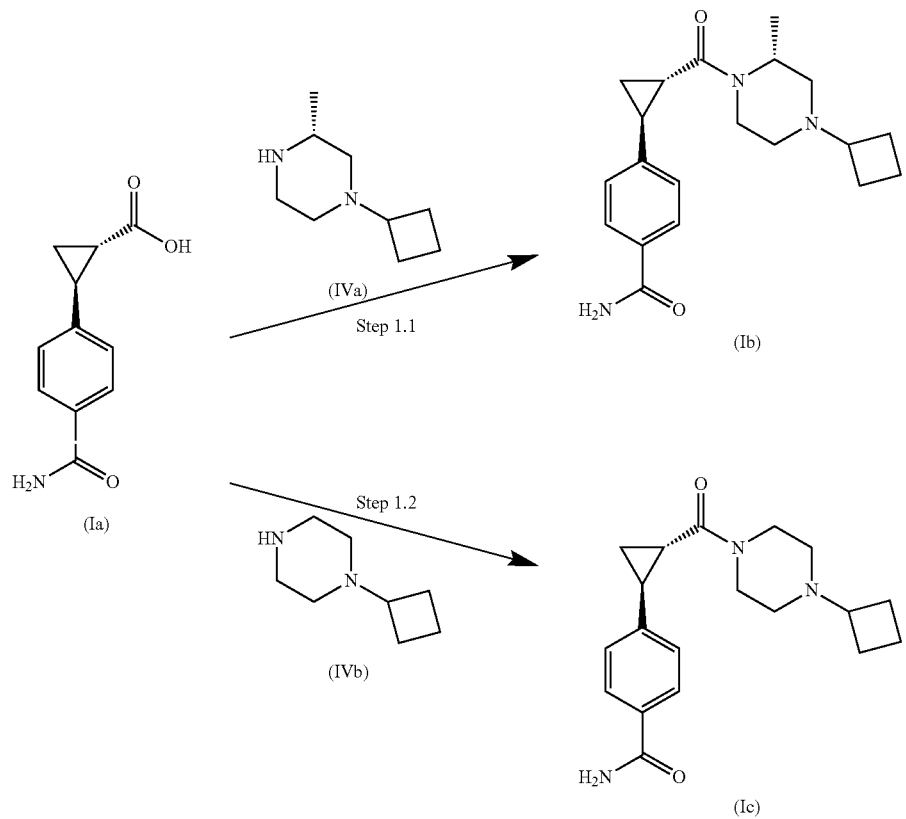

Step 1.1

A compound in accordance with formula Ib can be obtained by treating a compound in accordance with formula Ia, with a suitable activating agent, such as, for example, 1,1'-carbonyldiimidazole, in a suitable solvent, such as, for example, tetrahydrofuran, chloroform, dimethylformamide, 2-methyl-tetrahydrofuran, or mixtures of two or more thereof, and subsequently adding a compound in accordance with formula IVa or a suitable salt thereof, such as, for example, the dihydrochloride, and a suitable base, such as, for example, triethylamine or diisopropylethylamine.

In one embodiment, a compound in accordance with formula Ib can be obtained by treating a compound in accordance with formula Ia, with a compound of formula IVa or a suitable salt thereof, such as, for example, the dihydrochloride, in the presence of a suitable base, such as, for example, N-methylmorpholine, diisopropylethylamine, or triethylamine and a suitable activating agent, such as, for example, O-(7-azabenzotriazol-1-yl)-N,N,N',N'-tetramethyluronium hexafluorophosphate, O-(benzotriazol-1-yl)-N,N,N',N'-tetramethyluronium hexafluorophosphate, 1,1'-carbonyldiimidazole, or a mixture of 1-hydroxybenzotriazole and 1-ethyl-3-(3-dimethylaminopropyl)carbodiimide hydrochloride, in a suitable solvent, such as, for example, dimethylformamide, Me-THF, water, or mixtures thereof.

Step 1.2

A compound in accordance with formula Ic can be obtained by treating a compound in accordance with formula Ia, with a compound of formula IVb or a suitable salt thereof, such as, for example, the dihydrochloride, in the presence of a suitable base, such as, for example, N-methylmorpholine or diisopropylethylamine, and a suitable activating agent, such as, for example, O-(7-azabenzotriazol-1-yl)-N,N,N',N'-tetramethyluronium hexafluorophosphate, O-(benzotriazol-1-yl)-N,N,N',N'-tetramethyluronium hexafluorophosphate, or a mixture of 1-hydroxybenzotriazole and 1-ethyl-3-(3-dimethylaminopropyl)carbodiimide hydrochloride, in a suitable solvent, such as, for example, dimethylformamide, dimethylsulphoxide, water, or mixture thereof.

In one embodiment, a compound in accordance with formula Ic can be obtained by treating a compound in accordance with formula Ia, with a suitable activating agent, such as, for example, 1,1'-carbonyldiimidazole, in a suitable solvent, such as, for example, tetrahydrofuran, chloroform, dimethylformamide, 2-methyl-tetrahydrofuran, or mixture of two or more thereof, and subsequently adding a compound in accordance with formula IVb or a suitable salt thereof, such as, for example, the dihydrochloride, and a suitable base, such as, for example, triethylamine or diisopropylethylamine.

One aspect of the invention is a compound of formula Ia, or a pharmaceutically acceptable salt thereof,

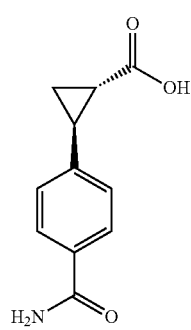

(Ia)

to be used as an intermediate for the preparation of the compounds of formula Ib and Ic.

EXAMPLES

The invention is further defined in the following Examples. It should be understood that the Examples are given by way of illustration only. From the above discussion and the Examples, one skilled in the art can ascertain the essential characteristics of the disclosure, and without departing from the spirit and scope thereof, can make various changes and modifications to adapt the disclosure to various uses and conditions. As a result, the disclosure is not limited by the illustrative examples set forth hereinbelow.

All temperatures are in degrees Celsius (° C.) and are uncorrected.

Unless otherwise noted, commercial reagents used in preparing the example compounds were used as received without additional purification.

Unless otherwise noted, the solvents used in preparing the example compounds were commercial anhydrous grades and were used without further drying or purification.

All starting materials are commercially available, unless stated otherwise.

The following abbreviations may be employed herein: CBS: Corey-Bakshi-Shibata; $^{13}$C NMR: carbon nuclear magnetic resonance; d: doublet; DMF: N,N-dimethyl formamide; DMSO: dimethyl sulfoxide; EDClxHCl: 1-ethyl-3-(3-dimethylaminopropyl) carbodiimide hydrochloride; ES: electrospray; g: gram; h: hour(s); $^{1}$H NMR: proton nuclear magnetic resonance; HPLC: high pressure liquid chromatography; kg: kilogram; L: liter; m: multiplet; M: molar; mL: milliliter; MHz: megahertz; min: minute(s); mmol: millimole; mol: mole; MS: mass spectrometry; NMM: N-methyl-morpholine; ppm: parts per million; s: singlet; 2-MeTHF: 2-methyl-tetrahydrofuran; br.: broad; Bu: butyl; calcd: calculated; Celite®: brand of diatomaceous earth filtering agent, registered trader of Celite Corporation; d: doublet; dd: doublet of doublet; ddd: doublet of doublet of doublet; dddd: doublet of doublet of doublet of doublet; DABCO: 1,4-diazabicyclo [2.2.2]octane; DCE: dichloroethane; DCM: dichloromethane; DIPEA: N-ethyl-N-isopropylpropan-2-amine; DME: dimethyl ether; DMEA: dimethyl ethylamine; dq: doublet of quartet; dt: doublet of triplet; EDC: 1-ethyl-3-(3-dimethylaminopropyl) carbodiimide hydrochloride; ESI: electrospray ion source; EtOAc: ethyl acetate; EtOH: ethanol; g: gram; h: hour(s); HBTU: O-Benzotriazole-N,N,N',N'-tetramethyl-uronium-hexafluoro-phosphate; HOBT: N-Hydroxybenzotriazole; HRMS: high resolution mass spectrometry; iPrOH: iso-propanol; MeOH: methanol; mg: milligram; MgSO$_4$: anhydrous magnesium sulfate (drying agent); MPLC: medium pressure liquid chromatography; MTBE: methyl tert-butyl ether; NaHCO$_3$: sodium bicarbonate; NH$_4$Cl: ammonium chloride; q: quartet; quin: quintet; rt: room temperature; sat: saturated; t: triplet; TEA: triethylamine; tBuOH: tert-butanol; td: triplet of doublet; TFA: trifluoroacetic acid; and THF: tetrahydrofuran.

The mass spectra were recorded on a Waters MS consisting of an Alliance 2795 (LC (mobile phase: 5-90% B; A: H$_2$O with 0.1% formic acid, B: CH$_3$CN, 8.6 min run) on Xbridge C18 column, 3.0×50 mm, 2.5 µm particle size) and Waters Micromass ZQ detector at 120° C. The mass spectrometer was equipped with an electrospray ion source (ESI) operated in a positive or negative ion mode. The mass spectrometer was scanned between m/z 120-800.

The $^{1}$H NMR spectra were recorded on a Bruker UltraShield Advance 400 MHz/54 mm spectrometer and processed with XWIN-NMR version 2.6 software. The chemical shifts (δ) are reported in parts-per-million from the deuterated solvent used.

The $^{13}$C NMR spectra were recorded on a Bruker UltraShield Advance 125 MHz/54 mm spectrometer and processed with XWIN-NMR version 2.6 software. The chemical shifts (δ) are reported in parts-per-million from the deuterated solvent used.

Example 1

(R)-1-(4-Bromo-phenyl)-2-chloro-ethanol

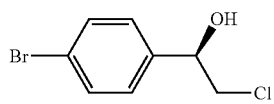

Borane dimethylsulfide (2.0 kg, 24.8 moles, 94% w/w) was mixed in toluene (8 L) at $t_{jacket}$=20° C. (R)-(+)-Methyl-CBS-oxazaborolidine (2.6 kg, 2.74 moles, 1M) as a toluene solution was added. The charging vessel was rinsed with toluene (0.5 L) and $t_{jacket}$ was set to 45° C. 1-(4-Bromo-phenyl)-2-chloro-ethanone (7.84 kg, 33.6 moles), which is commercially available from Jiangyan Keyan Fine Chemical Co. Ltd, was dissolved in 2-MeTHF (75 L) in a separate vessel and when $t_{inner}$ was above 40° C. in the first vessel, the 2-MeTHF solution was added during 3 h. The latter vessel was rinsed with 2-MeTHF (2 L) and added to the reaction mixture, which was left stirring at $t_{jacket}$=45° C. for 1 h. Analysis of a sample on HPLC indicated full conversion at this point using the following gradient method (mobile phase 20-95% B; A: 5% $CH_3CN$ in $H_2O$ with 0.1% TFA, B: 95% $CH_3CN$ in $H_2O$ with 0.085% TFA, 10 min run) on Chromolith Performance RP-18e, 4.6×100 mm. The reaction mixture was cooled to $t_{jacket}$=10° C. before slow quench with MeOH (36 L). The first liter of MeOH was added during 30 min. and the rest during additional 30 min. MeOH was distilled off under vacuum at $t_{jacket}$=50° C. The organic solution left was cooled to $t_{jacket}$=20° C., washed with 1M HCl in $H_2O$ (7 L conc HCl+73 L $H_2O$) and concentrated under vacuum at $t_{jacket}$=50° C. to approximately 40 L. Example 1 obtained in a 2-MeTHF solution can be stored at 10° C. for 20 h or used directly in the next synthetic step.

Example 2

(R)-2-(4-Bromo-phenyl)-oxirane

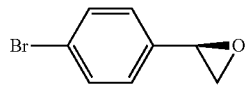

Aliquat® 175 (methyl tributyl ammonium chloride) (1.12 kg, 4.75 moles) was added to Example 1 as a 2-MeTHF solution (33.6 moles, 40 L) at $t_{jacket}$=20° C. NaOH (5.1 kg, 57.4 moles, 45% w/w) diluted in $H_2O$ (2 L) was added during 20 min. The reaction mixture was left stirring at $t_{jacket}$=20° C. for 2 h. Analysis of a sample on HPLC indicated full conversion at this point using the following gradient method (mobile phase 20-95% B; A: 5% $CH_3CN$ in $H_2O$ with 0.1% TFA, B: 95% $CH_3CN$ in $H_2O$ with 0.085% TFA, 10 min run) on Chromolith Performance RP-18e, 4.6×100 mm. The aq. phase was separated off and the organic phase washed with $H_2O$ (2×25 L). 2-MeTHF (25 L) was added and the organic phase concentrated under vacuum at $t_{jacket}$=50° C. to approximately 30 L. Example 2 obtained in a 2-MeTHF solution, can be stored at 5° C. for 140 h or used directly in the next synthetic step.

Example 3

(1S,2S)-2-(4-Bromo-phenyl)-cyclopropanecarboxylic acid

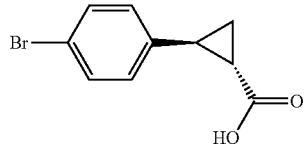 [SMILES: O=C(O)[C@H]1C[C@@H]1c1ccc(Br)cc1]

Triethyl phosphonoacetate (10.5 L, 51.9 moles, 98% w/w) was dissolved in 2-MeTHF (14 L) at $t_{jacket}$=−20° C. Hexyl lithium in hexane (21 L, 48.3 moles, 2.3 M) was added at a rate to maintain $t_{inner}$ below 0° C. The charging vessel was rinsed with 2-MeTHF (3 L) and the reaction solution was left stirring at $t_{jacket}$=10° C. Example 2 as a 2-MeTHF solution (33.6 moles, 30 L) was added during 20 min. The charging vessel was rinsed with 2-MeTHF (2 L) and the reaction solution was left stirring at $t_{jacket}$=65° C. for at least 16 h with the last 3 h at $t_{jacket}$=75° C. Analysis of a sample on HPLC using the following gradient method (mobile phase 20-95% B; A: 5% $CH_3CN$ in $H_2O$ with 0.1% TFA, B: 95% $CH_3CN$ in $H_2O$ with 0.085% TFA, 10 min run) on Chromolith Performance RP-18e, 4.6×100 mm indicated full conversion to the intermediate (1S,2S)-2-(4-bromo-phenyl)-cyclopropanecarboxylic acid ethyl ester. The reaction solution was cooled to $t_{jacket}$=20° C. NaOH (7.6 kg, 85.5 moles, 45% w/w) diluted in $H_2O$ (12 L) was added over 20 min. The reaction solution obtained was left stirring at $t_{jacket}$=60° C. for at least 2 h. Analysis of a sample on HPLC indicated full conversion at this point using the following gradient method (mobile phase 20-95% B; A: 5% $CH_3CN$ in $H_2O$ with 0.1% TFA, B: 95% $CH_3CN$ in $H_2O$ with 0.085% TFA, 10 min run) on Chromolith Performance RP-18e, 4.6×100 mm. The reaction solution was cooled to $t_{jacket}$=20° C., the aq. phase was separated off and the organic phase was extracted with $H_2O$ (37 L). The combined aq. phases were acidified to pH<3.5 with $H_3PO_4$ (9 L, 131 moles, 85% w/w) diluted in $H_2O$ (12.5 L). Only 17 L of the diluted $H_3PO_{4\ (aq)}$ was used to achieve the pH<3.5. The acidic aq. phase was extracted with 2-MeTHF (2×15 L). The combined organic phases including rinsing with 2-MeTHF (2 L) were concentrated under vacuum at $t_{jacket}$=50° C. to approximately 11 L. The 2-MeTHF solution was diluted with EtOH (14.5 L) at $t_{jacket}$=35° C. and $H_2O$ (16 L) was added over 20 min. The reaction solution was cooled to $t_{jacket}$=28° C. Seed (16 g, 0.066 moles) was added and the solution was stirred for 2 h at $t_{jacket}$=28° C. The reaction mixture was cooled to $t_{jacket}$=0° C. over 6 h and left stirring for at least 1 h. Additional $H_2O$ (8 L) was added during 40 min. and the product was filtered off and washed with cold $H_2O$ (10 L). Drying under vacuum at 40° C. gave 6.18 kg Example 3 (21.5 moles, 84% w/w), 64% yield over four steps from 7.84 kg 1-(4-bromo-phenyl)-2-chloro-ethanone (33.6 moles).

Recrystallization of Example 3: Two batches of Example 3 (6.18+7.04 kg) were mixed in EtOH (52 L) and heated at $t_{jacket}$=70° C. $H_2O$ (52 L) was added. The reaction solution was cooled to $t_{jacket}$=30° C. over 2.5 h. $H_2O$ (16 L) was added during 20 min. and the crystallization was cooled to $t_{jacket}$=20° C. during 3 h. The product was filtered off and washed with a mixture of $H_2O$ (8 L) and EtOH (2 L). Drying under vacuum at 40° C. gave 10.0 kg Example 3 (41.5 moles, 88% w/w), which was redissolved in toluene (39 L) and isooctane (57 L) at $t_{jacket}$=60° C. A clear solution was obtained. The reaction solution was cooled to $t_{jacket}$=45° C. and left stirring for 1 h, then cooled to $t_{jacket}$=20° C. over 2 h. The product was filtered off and washed with a mixture of toluene (4 L) and isooctane (36 L) in two portions. Drying under vacuum at 40° C. gave 7.4 kg Example 3 (29.8 moles, 97% w/w), 44% yield over four steps from 7.84+7.93 kg 1-(4-bromo-phenyl)-2-chloro-ethanone (67.5 moles). $^1$H-NMR (DMSO-$d_6$): δ 12.36 (s, 1H), 7.44 (d, 2H, J=8 Hz), 7.13 (d, 2H, J=8 Hz), 2.39 (m, 1H), 1.81 (m, 1H), 1.43 (m, 1H), 1.33 (m, 1H); $^{13}$C-NMR (DMSO-$d_6$): δ 173.76, 139.88, 131.20, 128.24, 119.14, 24.73, 24.31, 16.78; LC-MS (ESI): m/z 239 (M−1 ($Br^{79}$)) and 241 (M−1 ($Br^{81}$)). $R_t$=5.03 min with analytical method (mobile phase: 5-90% B; A: $H_2O$ with 0.1% formic acid, B: $CH_3CN$, 8.6 min run) on Xbridge C18, 3.0×50 mm, 2.5 μm particle size. The product was analyzed on a chiral column with UV-detection using isocratic method (mobile phase: EtOH/Isohexane/TFA (15/85/0.1 v/v/v)) on Kromosil 3-Amycoat, 150×4.6 mm, 3 μm particle size, giving an enantiomeric purity of 98.9% ee, $R_t$=5.29 min (isomer 1) and 5.97 min (isomer 2).

Example 4

(1S,2S)-2-(4-Cyano-phenyl)-cyclopropanecarboxylic acid

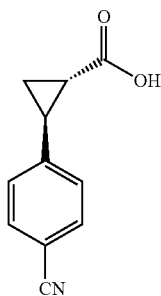 [SMILES: N#Cc1ccc([C@H]2C[C@@H]2C(=O)O)cc1]

Example 3 (3.7 kg, 14.9 moles, 97% w/w) and zinc-dust (98%+, <10 μm) (99 g, 1.51 moles) were mixed with DMF (13.5 L) and the slurry was stirred at $t_{jacket}$=20° C. The mixture was inerted and left with $N_2$ pressure of 0.1-0.2 bar. Bis(tri-t-butylphosphine)palladium (0) (27.5 g, 0.054 moles) was added to the slurry, and the vessel was inerted and left with $N_2$ pressure of 0.1-0.2 bar. The mixture was heated to $t_{jacket}$=45° C., $Zn(CN)_2$ (1.0 kg, 8.52 moles) was added to the suspension in one portion, and the system was inerted and left with $N_2$ pressure of 0.1-0.2 bar (N.B. Cyanide salts are highly toxic). The resulting mixture was heated to $t_{jacket}$=75° C. and stirred for at least 2 h. Analysis of a sample on HPLC indicated full conversion at this point using the following gradient method (mobile phase 20-95% B; A: 5% $CH_3CN$ in $H_2O$ with 0.05% formic acid, B: 95% $CH_3CN$ in $H_2O$ with 0.05% formic acid, 8 min run) on Chromolith Performance RP-18e, 4.6×100 mm. The reaction mixture was cooled to $t_{jacket}$=20° C. Thiol-functionalized silica (Silicycle, SiliaBond Thiol) (1.07 kg, 28% w/w) was added and the vessel was inerted. The reaction mixture was stirred for at least 36 h at $t_{jacket}$=20° C. The scavenger was filtered off via a filter with activated charcoal or equivalent (pall-filter). The vessel and the filter system were washed with 2-MeTHF (53 L). The filtrate and washings were combined and stirred at $t_{jacket}$=5° C. A pale yellow liquid resulted. NaCl (3.5 kg) in $H_2O$ (16.4 L) was added during 15 min. at such a rate so the inner temperature remained below 15° C. The resulting reaction mixture was heated to $t_{jacket}$=45° C. and the aq. phase was separated off. The organic phase was washed with $NaHSO_4 \times H_2O$ in $H_2O$ (2×(2.87 kg+16.4 L)) and NaCl in $H_2O$ (3.5 kg+16.4 L). The organic phase was cooled to $t_{jacket}$=10° C. and NaOH (1.54 kg, 19.3 moles, 50% w/w) diluted in $H_2O$ (41 L) was added during 45 min. The resulting reaction mixture was heated to $t_{jacket}$=30° C. and the organic phase separated off. The aq. phase was stirred at t ° C. $t_{jacket}$=20° C. and pH adjusted to 6.5 with $H_3PO_4$ (0.90 kg, 7.81 moles, 85% w/w) diluted in $H_2O$ (5.3 L) at a rate that maintained the inner temperature below 25° C. 2-MeTHF and $H_2O$ were distilled off under vacuum until a volume 85-90% of the volume prior to distillation, approximately 8 L. The reaction mixture was cooled to $t_{jacket}$=0° C. and continued charging off $H_3PO_4$ (1.17 kg, 10.1 moles, 85% w/w) diluted in $H_2O$ (8.2 L) until pH=4. The slurry was left stirring overnight at $t_{jacket}$=10° C. The product was filtered off, washed with $H_2O$ (2×4 L). Drying under vacuum at 40° C. gave Example 4 (2.24 kg, 11.2 moles, 93.2% w/w), 75% yield. $^1$H-NMR (DMSO-$d_6$): δ 12.45 (s, 1H), 7.72 (d, 2H, J=8 Hz), 7.37 (d, 2H, J=8 Hz), 2.50 (m, 1H), 1.94 (m, 1H), 1.50 (m, 1H), 1.42 (m, 1H); $^{13}$C-NMR (DMSO-$d_6$): δ 173.51, 146.68, 132.27, 126.93, 118.97, 108.85, 25.16, 25.04, 17.44; LC-MS (ESI): m/z 186 (M−1). $R_t$=3.63 min with analytical method (mobile phase: 5-90% B; A: $H_2O$ with 0.1% formic acid, B: $CH_3CN$, 8.6 min run) on Xbridge C18, 3.0×50 mm, 2.5 μm particle size.

Example 5

(1S,2S)-2-(4-Carbamoyl-phenyl)-cyclopropanecarboxylic acid

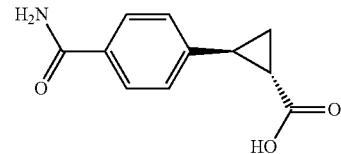

Example 4 (4.46 kg, 22.0 moles, 92.5% w/w) was mixed in $H_2O$ (40 L) at $t_{jacket}$=30° C. NaOH (2.25 kg, 28.1 moles, 50% w/w) diluted in $H_2O$ (6 L) was added at such a rate so $t_{inner}$ remained below 35° C. The charging vessel was rinsed with $H_2O$ (1 L). If the pH was not ≥12, more NaOH was charged in the same concentration as previously. Hydrogen peroxide (4.89 kg, 50.3 moles, 35% w/w) was added at a rate to maintain $t_{inner}$ below 35° C. The charging vessel was rinsed with $H_2O$ (1 L) and the reaction slurry was left stirring for 0.5-1.0 h. Analysis of a sample on HPLC indicated full conversion at this point using the following gradient method (mobile phase 20-95% B; A: 5% $CH_3CN$ in $H_2O$ with 0.05% formic acid, B: 95% $CH_3CN$ in $H_2O$ with 0.05% formic acid, 8 min run) on Chromolith Performance RP-18e, 4.6×100 mm. The reaction mixture was cooled to $t_{jacket}$=0° C. and left stirring for at least 0.5 h when the temperature was reached. The sodium salt of Example 5 was filtered off and washed with cold $H_2O$ (2×7 L). The solid was slurry washed on the filter with $NaHSO_4 \times H_2O$ (2.76 kg, 20.0 moles) diluted in $H_2O$ (35 L). The slurry was kept stirring at $t_{jacket}$=0° C. for 1 h. If the pH was not <3.7, it was adjusted with NaHSO$_4$×H$_2$O in H$_2$O. The product was filtered off, washed with cold H$_2$O (3×14 L). Drying under vacuum at 40° C. gave Example 5 (4.0 kg, 18.2 moles, 93.4% w/w), 83% yield. $^1$H-NMR (DMSO-d$_6$): δ 12.40 (s, 1H), 7.94 (s, 1H), 7.79 (d, 2H, J=8 Hz), 7.32 (s, 1H), 7.23 (d, 2H, J=8 Hz), 2.44 (m, 1H), 1.88 (m, 1H), 1.47 (m, 1H), 1.39 (m, 1H); $^{13}$C-NMR (DMSO-d$_6$): δ 173.83, 167.67, 143.94, 132.17, 127.68, 125.73, 25.21, 24.67, 17.11; LC-MS (ESI): m/z 206 (M+1). R$_t$=2.13 min with analytical method (mobile phase: 5-90% B; A: H$_2$O with 0.1% formic acid, B: CH$_3$CN, 8.6 min run) on Xbridge C18, 3.0×50 mm, 2.5 μm particle size. The product was analyzed on a chiral column with UV-detection using isocratic method (mobile phase: EtOH/Isohexane/TFA (15/85/0.1 v/v/v)) on Kromosil 3-Amycoat, 150×4.6 mm, 3 μm particle size, giving an enantiomeric purity of >99% ee, R$_t$=13.40 min (isomer 1) and 22.22 min (isomer 2).

Example 6

(R)-1-Cyclobutyl-3-methylpiperazine×2HCl

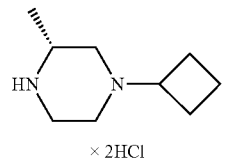

(R)-Boc-2-methylpiperazine (350 g, 1.71 moles, 98% w/w), which is commercially available from Lanzhou Boc Chemical Co., was dissolved in EtOH (2.75 L) at t$_{jacket}$=20° C. Acetic acid (1.37 L) was added in one portion followed by the addition of cyclobutanone (184 g, 2.57 moles). The charging vessel was rinsed with EtOH (250 mL) and the light yellow solution was left stirring at t$_{jacket}$=20° C. for 1 h. NaBH(OAc)$_3$ (497 g, 2.48 moles, 95% w/w) was added in 20 portions over 90 min. EtOH (340 mL) was used for rinsing. The reaction mixture was left stirring for 2 h. A sample was analyzed on GC using HP-5MS column (length 25 m, ID 0.32 mm, Film 0.52 μm) with a gradient method (2 min at 60° C., followed by 25° C./min during 8 min then 2 min at 260° C.). Frontinlet temperature=200° C. using He as gas and a detector temperature=300° C. More NaBH(OAc)$_3$ (30 g, 0.14 moles) was added to complete the reaction within 1 h. The reaction mixture was cooled to t$_{jacket}$=0° C. before quenching with 5M NaOH (5.5 L). EtOH was distilled off under vacuum at t$_{jacket}$=50° C. The H$_2$O phase was extracted with toluene (5.5 L) at t$_{jacket}$=20° C. The organic phase was combined with a second batch, started with (R)-Boc-2-methylpiperazine (300 g, 1.47 moles, 98% w/w). The combined organic phases were concentrated under vacuum at t$_{jacket}$=50° C. to approximately 2 L. The obtained toluene solution with the intermediate can be stored at 5° C. for several days. The toluene solution was diluted with 2-propanol (2 L) at t$_{jacket}$=10° C., and HCl in 2-propanol (1.06 L, 6.36 moles, 6M) diluted in 2-propanol (2 L) was added over 30 min. The reaction solution was heated to t$_{jacket}$=48° C. HCl in 2-propanol (2.12 L, 12.72 moles, 6M) diluted in 2-propanol (2 L) was added over 2 h at t$_{inner}$=46° C. The reaction solution was kept at t$_{jacket}$=48° C. for an additional 3 h before being cooled to t$_{jacket}$=0° C. over 1 h. A seed mixture (0.4 L reaction solution with Example 6 (0.2 g, 0.89 mmoles) was added. The reaction mixture was left stirring at t$_{jacket}$=0° C. overnight and the product was filtered off. Drying under vacuum at 40° C. gave Example 6 (620 g, 2.63 moles, 96.3% w/w), 83% yield. $^1$H-NMR (DMSO-d$_6$): δ 12.46 (s, 1H), 10.13 (s, 2H), 3.35-3.74 (m, 6H), 3.09 (m, 1H), 2.92 (m, 1H), 2.39 (m, 2H), 2.16 (m, 2H), 1.72 (m, 2H), 1.32 (d, 3H, J=6.4 Hz); $^{13}$C-NMR (DMSO-d$_6$): δ 58.50, 49.62, 48.13, 44.30, 24.48, 24.38, 15.25, 13.26

Example 7

4-{(1S,2S)-2-[((R)-4-Cyclobutyl-2-methylpiperazin-1-yl)carbonyl]-cyclopropyl}-benzamide

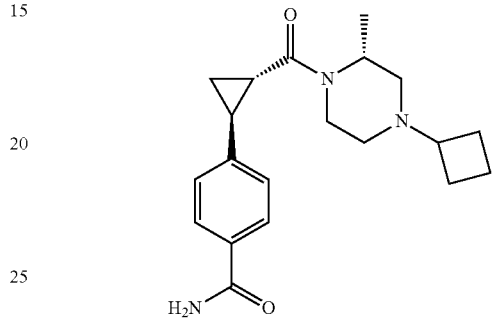

Example 5 (10.0 g, 48.7 mmoles) was mixed in 2-MeTHF (200 mL) at t$_{jacket}$=25° C. 1,1'-Carbonyldiimidazole (11.0 g, 53.6 mmoles, 82.1% w/w) was added in 1 portion. The reaction slurry was slowly heated to t$_{jacket}$=85° C. and after approximately 5 h the reaction slurry was cooled to t$_{reaction\ mixture}$=25° C. Example 6 (13.8 g, 58.5 mmoles) and TEA (7.55 mL, 53.6 mmoles) were added to the reaction slurry. The reaction slurry was heated at t$_{jacket}$=70° C. for 3 h. Analysis of a sample on HPLC indicated full conversion at this point using the gradient method (mobile phase 20-95% B; A: 5% CH$_3$CN in H$_2$O with 0.1% TFA, B: 95% CH$_3$CN in H$_2$O with 0.085% TFA, 10 min run) on Chromolith Performance RP-18e, 4.6×100 mm. The reaction slurry was cooled to t$_{jacket}$=40° C. 1M Na$_2$CO$_3$ in brine (90 mL) was added. The aq. phase was separated off and the organic phase was washed with brine (2 L). The assay of Example 7 in the organic phase was determined by $^1$H NMR and the volume of the organic phase was adjusted to 10 relative volumes (15.4 g of Example 7). The organic phase was cooled to t$_{jacket}$=15° C. and extracted with 10% H$_3$PO$_4$ in H$_2$O (charged until pH 2.5, 110 mL). The lower aq. phase was collected and the remaining organic phase was re-extracted with 10% H$_3$PO$_4$ in H$_2$O (50 mL). The combined aq. phases were basified to pH>12 with 5M KOH and extracted with MeTHF twice (200 mL, 50 mL). The combined organic phases were extracted with brine (50 mL) and filtered to remove inorganic salts. The assay of Example 7 in the organic phase was determined by $^1$H NMR and the volume of the organic phase was reduced to 6 relative volumes (14.4 g of Example 7, 86 mL). Crystallisation was performed starting at T$_{jacket}$=55° C. After cooling to t$_{jacket}$=40° C., heptane (21.6 mL) as well as seed (128 mg of Example 7) was added. The mixture was after aging cooled down to t$_{jacket}$=20° C., when a second addition of heptane (64.8 mL) was performed. The product was filtered off and washed with MeTHF/Heptane twice (2*30 mL). Drying under vacuum at 40° C. gave 12.6 g Example 7 (35.2 mmoles, 98.7% w/w, 75% yield). $^1$H-NMR (DMSO-d$_6$): δ 7.91 (br s, 1H), 7.78 (d, J=8.4 Hz, 2H), 7.30 (br s, 1H), 7.25 (d, J=8.0 Hz, 2H), 4.54 and 4.36 (br s, 1H), 4.17 and 4.01 (d, J=12.2 Hz, 1H), 3.20 and 2.80 (t, J=11.9 Hz, 1H), 2.74 (d, J=11.4 Hz, 1H), 2.67-2.55 (m, 2H), 2.33 (br s, 2H), 1.99-1.88 (m, 2H), 1.88-1.53 (m, 6H), 1.48-1.37 (m, 1H), 1.27 (br s, 3H), 1.12 (br s, 1H); LC-MS (ESI): m/z 342 (M+1). $R_t$=1.68 min with analytical method (mobile phase: 5-90% B; A: $H_2O$ with 0.1% formic acid, B: $CH_3CN$, 8.6 min run) on Xbridge C18, 3.0×50 mm, 2.5 μm particle size. The LC purity of the product was analyzed on an Atlantis T3 column (3.0×150 mm, 3.0 μm particle size) with UV-detection (250 nm) using a gradient method (mobile phase 2-50% B; A: $H_2O$ with 0.03% TFA, B: $CH_3CN$ with 0.03% TFA, 30 min run), giving a purity of 99.48 area % at 12.06 min. The product was analyzed on chiral SFC (UV detection) using isocratic method (mobile phase: 55% EtOH with 0.1% DMEA, supercritical $CO_2$) on ChiralPak AD-H, 10×250 mm, 5 μm particle size, giving an enantiomeric purity of >99% ee, $R_t$=1.98 min.

Example 8

1-Cyclobutylpiperazine×2HCl

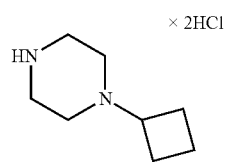

N-Boc-piperazine (46 g, 0.25 moles), which is commercially available from SAFC, was dissolved in EtOH (415 mL) at $t_{jacket}$=20° C. Acetic acid (140 mL) was added in one portion followed by the addition of cyclobutanone (26.5 g, 0.37 moles). The charging vessel was rinsed with EtOH (25 mL) and the light yellow solution was left stirring at $t_{jacket}$=20° C. for 1 h. NaBH(OAc)$_3$ (80 g, 0.36 moles, 95% w/w) was added in 20 portions over 2 h. EtOH (25 mL) was used for rinsing. The reaction mixture was left stirring for 2 h. The sample analyzed on GC indicated full conversion at this point using HP-5MS column (length 25 m, ID 0.32 mm, Film 0.52 μm) with a gradient method (2 min at 60° C., followed by 25° C./min during 8 min then 2 min at 260° C.). Front inlet temperature=200° C. using He as gas and a detector temperature=300° C. NAOH (296 g, 3.70 moles, 50% w/w) diluted in $H_2O$ (230 mL) was added at such a rate so $t_{inner}$ remained below 35° C.

EtOH was distilled off under vacuum at $t_{jacket}$=45° C. to approximately 650 mL. The water phase was extracted with toluene (550 mL) at $t_{jacket}$=45° C. and the obtained organic phase was concentrated under vacuum at $t_{jacket}$=45° C. to approximately 250 mL. The toluene solution was diluted with 2-propanol (140 mL) at $t_{jacket}$=20° C. and $H_2O$ (2.2 mL, 0.12 moles) was added. HCl in 2-propanol (82 mL, 0.49 moles, 6M) diluted in 2-propanol (140 mL) was added over 30 min at $t_{jacket}$=20° C. The reaction solution was heated to $t_{jacket}$=48° C. HCl in 2-propanol (164 mL, 0.99 moles, 6M) diluted in 2-propanol (276 mL) was added over 2 h at $t_{inner}$=46° C. The reaction solution was kept at $t_{jacket}$=48° C. for an additional 4 h before cooling to $t_{jacket}$=10° C. over 1 h. The product was filtered off and washed with cold 2-propanol (2×230 mL). Drying under vacuum at 40° C. gave 44 g Example 8 (0.20 moles, 95.9% w/w), 80% yield. $^1$H-NMR (DMSO-d$_6$): δ 12.46 (s, 1H), 10.07 (s, 2H), 3.73 (m, 1H), 3.05-3.61 (m, 8H), 2.37 (m, 2H), 2.14 (m, 2H), 1.70 (m, 2H); $^{13}$C-NMR (DMSO-d$_6$): δ 58.05, 44.67, 39.59, 24.38, 13.18.

Example 9

4-{(1S,2S)-2-[(4-Cyclobutylpiperazin-1-yl)carbonyl]-cyclopropyl}-benzamide

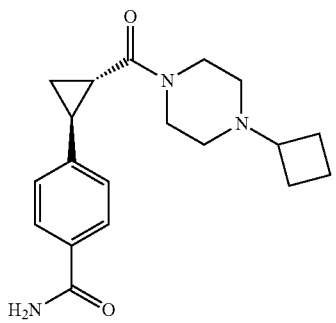 [SMILES: NC(=O)c1ccc([C@H]2C[C@@H]2C(=O)N2CCN(C3CCC3)CC2)cc1]

Example 5 (5.52 g, 26.7 mmoles, 99.1% w/w) and Example 8 (6.07 g, 28.0 mmoles, 98.40% w/w) were mixed in DMSO (82 mL) at $t_{jacket}$=22° C. N-Methylmorpholine (2.94 mL, 27.2 mmoles) was added over 5 min. The charging vessel was rinsed with DMSO (2.8 mL). HOBt/NMM solution (1.80 g, 2.66 mmoles, 20% w/w) was added in one portion. The charging vessel was rinsed with DMSO (2.8 mL). EDCl×HCl (7.16 g, 38.0 mmoles) was added over 10 min. at $t_{jacket}$=22° C. The reaction was complete after 2 h. For analysis the following gradient method was used (mobile phase 20-95% B; A: 5% $CH_3CN$ in $H_2O$ with 0.05% formic acid, B: 95% $CH_3CN$ in $H_2O$ with 0.05% formic acid, 8 min run) on Chromolith Performance RP-18e, 4.6×100 mm. The reaction solution was heated to 60° C. and pH adjusted with TEA (5.18 g g, 51.2 mmol) to pH~8. The solid mixture was cooled to 20° C. after which $H_2O$ (69.8 mL) was added and left to stir for 16 h. The product was filtered off, and slurry washed with cold $H_2O$ (2×33 mL). Drying under vacuum at 40° C. gave 7.53 g Example 9 (22.8 mmoles, 99.0% w/w), 85% yield. $^1$H-NMR (DMSO-d$_6$): δ 7.91 (br s, 1H), 7.78 (d, J=8.0 Hz, 2H), 7.29 (br s, 1H), 7.24 (d, J=8.0 Hz, 2H), 3.68-3.39 (m, 4H), 2.72-2.62 (m, 1H), 2.40-2.29 (m, 2H), 2.26-2.12 (m, 4H), 1.99-1.88 (m, 2H), 1.83-1.70 (m, 2H), 1.67-1.56 (m, 2H), 1.47-1.39 (m, 1H), 1.28-1.20 (m, 1H); LC-MS (ESI): m/z 328 (M+1). $R_t$=1.62 min with analytical method (mobile phase: 5-90% B; A: $H_2O$ with 0.1% formic acid, B: $CH_3CN$, 8.6 min run) on Xbridge C18, 3.0×50 mm, 2.5 μm particle size. The LC purity of the product was analyzed on an Atlantis T3 column (3.0× 150 mm, 3.0 μm particale size) with UV-detection (250 nm) using a gradient method (mobile phase 2-50% B; A: $H_2O$ with 0.03% TFA, B: $CH_3CN$ with 0.03% TFA, 30 min run) giving a purity of 97.83 area % at 11.10 min. The chiral purity of the product was analyzed on a chiral column with UV-detection (250 nm) using isocratic method (mobile phase: Heptane/EtOH (80/20)+0.1% Diethylamine) on Chiralpak AD-H, 4.6×150 mm, giving an enantiomeric purity of >99% ee.

What is claimed is:

1. A process for preparing a compound of formula Ia:

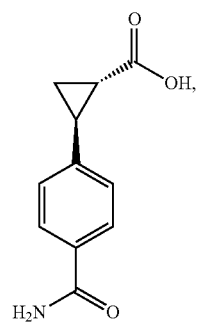

(Ia)

or a pharmaceutically acceptable salt thereof, wherein the process comprises reacting a compound of formula IX:

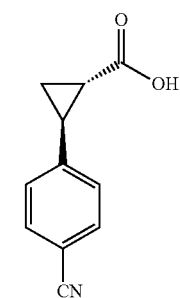

(IX)

with a base and a peroxide; and then reacting the resulting mixture with an acidic solution.

2. The process of claim 1, wherein said base is sodium hydroxide.

3. The process of claim 1, wherein said peroxide is hydrogen peroxide.

4. The process of claim 1, wherein said acidic solution is an aqueous solution of sodium hydrogen sulfate.

5. The process of claim 1, wherein:
the compound of formula IX is prepared by a process comprising reacting a compound of formula VIII:

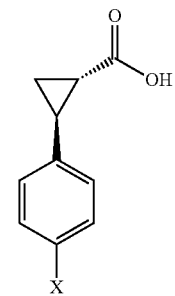

(VIII)

with a metal, a metal cyanide, and a catalyst; and
X is Cl, Br, or I.

6. The process of claim 5, wherein X is Br.

7. The process of claim 5, wherein said metal is zinc.

8. The process of claim 5, wherein said metal cyanide is zinc-(II)-cyanide.

9. The process of claim 5, wherein said catalyst is bis(tri-t-butylphosphine)palladium(0).

10. The process of claim 5, wherein the compound of formula VIII is prepared by a process comprising reacting a compound of formula VII:

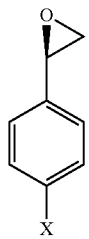

(VII)

with a mixture of a first base and a tri$C_{1-6}$alkyl phosphonoacetate, and then reacting the resulting mixture with a second base, wherein X is Cl, Br, or I.

11. The process of claim 10, wherein:
the compound of formula VII is prepared by a process comprising reacting a compound of formula VI:

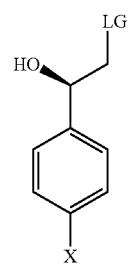

(VI)

with a base;
wherein LG is Cl, Br, I, tosylate, brosylate, nosylate, mesylate, or triflate; and
wherein X is Cl, Br, or I.

12. The process of claim 11, wherein the compound of formula VI is prepared by a process comprising reacting a compound of formula V:

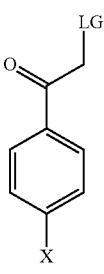

(V)

with a reducing agent and a chiral oxazaborolidine, wherein X is Cl, Br, or I; and LG is Cl, Br, I, tosylate, brosylate, nosylate, mesylate or triflate.

13. A process for preparing a compound of formula Ib, or a pharmaceutically acceptable salt thereof:

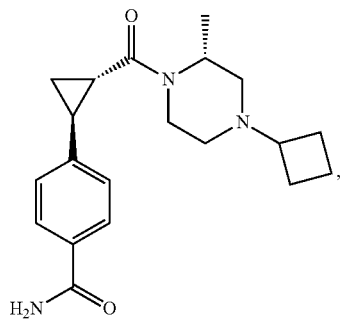
(Ib)

wherein:
the process comprises reacting a compound of formula Ia:

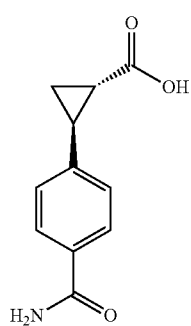
(Ia)

with an activating agent, and then reacting the resulting mixture with a compound of formula IVa, or a suitable salt thereof:

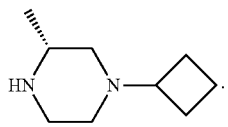
(IVa)

14. The process of claim 13, wherein said activating agent is 1,1'-carbonyldiimidazole.

15. The process of claim 13, wherein the compound of formula IVa, or suitable salt thereof, is prepared by a process comprising reacting a compound of formula IIIa:

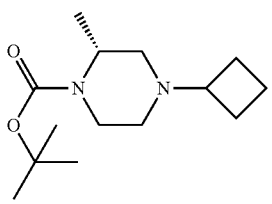
(IIIa)

with an acid.

16. The process of claim 15, wherein the compound of formula IIIa is prepared by a process comprising reacting a compound of formula IIa:

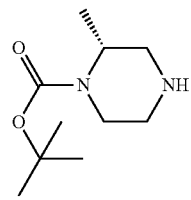
(IIa)

with cyclobutanone and a reducing agent.

17. A process for preparing a compound of formula Ic, or a pharmaceutically acceptable salt thereof:

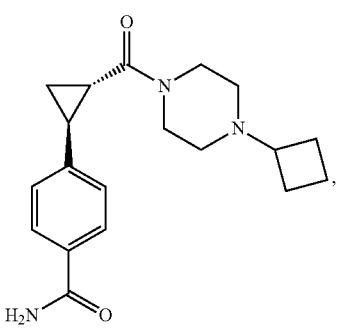
(Ic)

wherein:
the process comprises reacting a compound of formula Ia:

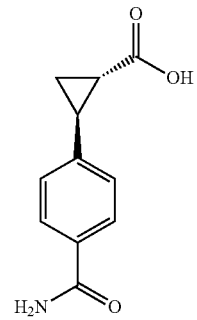
(Ia)

with an activating agent, and then reacting the resulting mixture with a compound of formula IVb, or a suitable salt thereof:

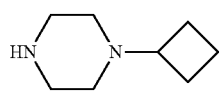
(IVb)

and a base.

18. The process of claim 17, wherein the activating agent is a mixture of 1-hydroxybenzotriazole and 1-ethyl-3-(3-dimethylaminopropyl)carbodiimide hydrochloride.

19. The process of claim 17, wherein the compound of formula IVb is prepared by a process comprising reacting a compound of formula IIIb:

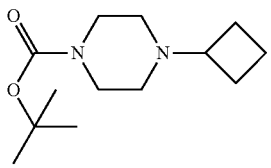

(IIIb)

with an acid.

20. The process of claim 15, wherein said acid is hydrochloric acid.

21. The process of claim 19, wherein the compound of formula IIIb is prepared by a process reacting a compound of formula IIb:

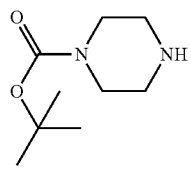

(IIb)

with cyclobutanone and a reducing agent.

22. The process of claim 16, wherein said reducing agent is sodium triacetoxy borohydride.

23. The process of claim 10, wherein said first base is alkyl lithium, and said second base is sodium hydroxide or lithium hydroxide.

24. The process of claim 11, wherein said base is sodium hydroxide or lithium hydroxide.

25. The process of claim 12, wherein said reducing agent is borane*THF or borane dimethylsulfide.

26. The process of claim 17, wherein said base is N-methylmorpholine or diisopropylethylamine.

27. The process of claim 19, wherein said acid is hydrochloric acid, trifluoroacetic acid, or sulfonic acid.

28. The process of claim 21, wherein said reducing agent is sodium triacetoxyborohydride or sodium cyanoborohydride.

* * * * *